US008962525B2

(12) United States Patent
Martin

(10) Patent No.: US 8,962,525 B2
(45) Date of Patent: Feb. 24, 2015

(54) STABLE FORMULATIONS CONTAINING FUMED ALUMINUM OXIDE

(71) Applicant: Timothy Martin, Ringoes, NJ (US)

(72) Inventor: Timothy Martin, Ringoes, NJ (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 14/351,974

(22) PCT Filed: Oct. 17, 2012

(86) PCT No.: PCT/US2012/060571
§ 371 (c)(1),
(2) Date: Apr. 15, 2014

(87) PCT Pub. No.: WO2013/059288
PCT Pub. Date: Apr. 25, 2013

(65) Prior Publication Data

US 2014/0274709 A1 Sep. 18, 2014

Related U.S. Application Data

(60) Provisional application No. 61/548,273, filed on Oct. 18, 2011.

(51) Int. Cl.

| | |
|---|---|
| ***A01N 25/22*** | (2006.01) |
| ***A01N 43/80*** | (2006.01) |
| ***A01N 43/70*** | (2006.01) |
| ***A01N 43/90*** | (2006.01) |
| ***A01N 43/824*** | (2006.01) |
| ***A01N 25/08*** | (2006.01) |

(52) U.S. Cl.
CPC ..................................... *A01N 25/22* (2013.01)
USPC ............ 504/134; 504/139; 504/363; 504/367

(58) Field of Classification Search
USPC ................................. 504/134, 139, 363, 367
See application file for complete search history.

(56) References Cited

U.S. PATENT DOCUMENTS 7,833,939 B2 * 11/2010 Takahashi et al. ............ 504/156
2010/0210704 A1 8/2010 Ohata et al.

FOREIGN PATENT DOCUMENTS

WO 9812923 A1 4/1998
WO 2009112486 A2 9/2009

* cited by examiner

*Primary Examiner* — John Pak
(74) *Attorney, Agent, or Firm* — FMC Corporation

(57) ABSTRACT

The present invention provides novel herbicidal aqueous suspoemulsion or aqueous suspension concentrate compositions containing an herbicidal active agent and fumed alumina as a stabilization agent that have superior chemical and physical stability as well as superior re-dispersion properties.

7 Claims, No Drawings

STABLE FORMULATIONS CONTAINING FUMED ALUMINUM OXIDE

FIELD OF THE INVENTION

The present invention relates to the field of agrochemical formulations.

BACKGROUND OF THE INVENTION

To enable the efficient elimination or controlling of unwanted plants, it is desirable to use effective chemical formulations of herbicides. Compositions containing two or more herbicides are desirable in agricultural, specialty applications and related endeavors due to broadening the spectrum or range of unwanted plant species killed or controlled.

Due to the desirability of having a composition with the above-mentioned properties, it is useful to use combinations of herbicides to obtain enhanced control of numerous weeds with a single herbicidal application. Combinations of pesticides are known and available as mixed solutions of the active ingredients in their commercially available formulations. One method of preparing such a composition is referred to as "tank mixing" in which the ingredients in their commercially available form are mixed together by the user in a quantity of water. Tank mixes require the end user to purchase two or more commercial formulations, store them, calculate the correct amount of each active ingredient, measure those amounts into the mix and when empty, properly dispose of a number of containers. Tank mixing two or three different commercial formulations often results in physical instabilities causing precipitation of active ingredients, flocculation, phase separation and the like, providing uneven distribution of the active ingredients. Combining active ingredients into one formulation is beneficial but frequently more complex due to widely different physical properties of the active ingredients in which chemical and physical stability are problems.

SUMMARY OF THE INVENTION

The present invention provides novel herbicidal aqueous suspoemulsion or aqueous suspension concentrate compositions containing an herbicidal active agent and fumed alumina as a stabilization agent that have superior chemical and physical stability as well as superior re-dispersion properties.

DETAILED DESCRIPTION OF THE INVENTION

The present invention provides novel herbicidal aqueous suspoemulsion or aqueous suspension concentrate compositions containing an herbicidal active agent and fumed alumina as a stabilization agent that have superior chemical and physical stability as well as superior re-dispersion properties.

In one aspect the present invention relates to a novel aqueous suspoemulsion composition containing an herbicidal agent comprised of atrazine, pyroxasulfone and fluthiacet-methyl that has superior chemical and physical stability as well as superior re-dispersion.

In particular the aqueous suspoemulsion composition of the present invention comprises:

i) an aqueous suspension concentrate composition containing pyroxasulfone and atrazine;

ii) an emulsion in water composition containing fluthiacet-methyl; and iii) fumed alumina.

Another embodiment of the present invention is a process for the preparation of an aqueous suspoemulsion composition comprising:

i) forming an aqueous suspension concentrate composition containing pyroxasulfone and atrazine;

ii) forming an emulsion in water composition containing fluthiacet-methyl;

iii) blending the suspension concentrate and emulsion in water compositions together and iv) adding fumed alumina and blending the mixture to form a homogenous mixture.

Still another embodiment of the present invention is a process for the preparation of an aqueous suspoemulsion composition comprising:

i) forming an aqueous suspension concentrate composition containing pyroxasulfone and atrazine and fumed alumina;

ii) forming an emulsion in water composition containing fluthiacet-methyl;

iii) blending the suspension concentrate and emulsion in water compositions together to form a homogenous mixture.

Another embodiment of the present invention is an aqueous suspension concentrate composition comprising:

i) an agriculturally active component comprising fluthiacet-methyl, atrazine and pyroxasulfone;

ii) a surfactant component comprising an acrylic graft copolymer and a polyalkylene oxide block copolymer;

iii) an antifoam agent;

iv) a biocide;

v) a pH adjusting agent;

vi) an antifreeze agent; and vii) fumed alumina.

It has been surprisingly discovered that the addition of fumed alumina to a suspoemulsion or suspension concentrate compositions provides exceptional physical and chemical stability to the compositions. Other stabilizing agents, for example, fumed silica, when used in the present suspoemulsion or suspension concentrate compositions, provide good chemical stability but lack physical stability (e.g. precipitates form after 24 hours at room temperature, re-dispersion difficulties). Adding fumed alumina to the present suspoemulsion or suspension concentrate compositions provides chemically and physically stable compositions. In preparing a suspoemulsion composition, fumed alumina can be added to the suspension concentrate composition portion, or may be added to the final formulation composition; preferably it is added to the suspension concentrate portion of the composition.

In one aspect of the present invention a suspoemulsion composition is formed by combining a suspension concentrate composition with an emulsion in water composition. A suspension concentrate (SC) is a formulation in which a solid active ingredient(s) is suspended in a liquid carrier. The aqueous suspension concentrate composition portion of the suspoemulsion further comprises a surfactant component, a pH adjuster (optional), an anti-freeze agent, an antifoam agent and an anti-microbial (biocide) agent. Atrazine is present in an amount of from 40% to 55% by weight, preferably in an amount of from 44% to 51% by weight of all the components in the SC composition. Pyraxosulfone is present in an amount of from 5% to about 7% by weight of all the components in the SC composition. The surfactant component is comprised of at least two surfactants; an alkyl EO/PO copolymer and an acrylic graft copolymer. The alkyl EO/PO copolymer is preferably, for example, TERGITOL™ XD Surfactant, available from Dow® Chemicals and is present in an amount of from 2% to 3% by weight of all the components in the SC composition. The acrylic graft copolymer is preferably, for example, TERSPERSE® 2500 Dispersant, available from Huntsman Performance Products and is present in amount of from 3% to 4% by weight of all the components in the SC composition. The pH adjuster is preferably an acid, for example, glacial acetic acid, and is present in an amount of from 0% to 0.13% by weight of all the components in the SC composition. The anti-freeze agent is preferably propylene glycol and is present in an amount of from 5% to 10% by weight, preferably 6% by weight of all the components in the SC composition. The antifoam agent is preferably a silicone emulsion, for example, DOWCORNING® AF Emulsion available from Dow® Chemical Company and is present in an amount of 0.05% to 0.5% by weight, preferably 0.1% by weight of all the components in the SC composition. The biocide is preferably, for example, KATHON™ CG or LEGEND® MK both available from Dow® Chemical Company or Acticide® MV available from Thor Specialties, Inc., and is present in an amount of from 0.05% to 0.5% by weight, preferably 0.1% by weight of all the components in the SC composition. The stabilization component is fumed alumina, preferably as an aqueous dispersion that is acidic, for example, AERODISP® W 630, available from Evonik Industries, and is present on an amount of from 0.5% to 2% by weight of all the components in the SC composition. The SC composition can further comprise a thickening agent, for example, magnesium aluminum silicate (Veegum® Magnesium Aluminum Silicate from R.T.Vanderbilt Company)

An emulsion in water (EW) is a formulation in which droplets of a non-water soluble phase (oil or non-water soluble solvent) is evenly distributed in water. The EW portion of the suspoemulsion composition of the present invention further comprises a solvent that is not water soluble, a surfactant component, a pH adjuster, an anti-freeze agent, an antifoam agent and an anti-microbial (biocide) agent. Fluthiacet-methyl is present in an amount of 1% to 2% by weight of all the components in the EW composition. The solvent is preferably an aromatic solvent, for example, Aromatic 200 or Aromatic 200 ND, available from ExxonMobil$^{tm}$ Chemicals, and is present in an amount of from 45% to 50% by weight of all the components in the EW composition. The surfactant component is comprised of at least two surfactants; a non-ionic polymeric surfactant and a polyalkylene oxide block copolymer. The non-ionic polymeric surfactant is preferably, for example, Atlox™ 4914, available from Crodia Crop Care and is present in an amount of from 4% to 5% by weight of all the components in the EW composition. The polyalkylene oxide block copolymer is preferably, for example, Atlas™ G-5000, available from Crodia Crop Care and is present in amount of from 4.5% to 5.5% by weight of all the components in the EW composition. The pH adjuster is preferably an acid, for example, glacial acetic acid, and is present in an amount of from 0.01% to 0.1% by weight of all the components in the EW composition. The anti-freeze agent is preferably propylene glycol and is present in an amount of from 5% to 10% by weight, preferably 6% by weight of all the components in the EW composition. The antifoam agent is preferably a silicone emulsion, for example, DOWCORNING® AF Emulsion available from Dow Chemical Company and is present in an amount of 0.05% to 0.5% by weight, preferably 0.1% by weight of all the components in the EW composition. The biocide is preferably, for example, KATHON™ CG or LEGEND® MK both available from Dow® Chemical Company or Acticide® MV available from Thor Specialties, Inc. and is present in an amount of from 0.05% to 0.1% by weight of all the components in the EW composition.

In another embodiment of the present invention an aqueous suspension concentrate is formed using fumed alumina as the stability agent. The aqueous suspension concentrate composition comprises an active ingredient component comprising fluthiacet-methyl, pyroxasulfone and atrazine; a surfactant component comprising an acrylic graft copolymer and a polyalkylene oxide copolymer; an antifoam agent; a biocide; a pH adjusting agent; an antifreeze agent; and a stabilization agent. Fluthiacet-methyl is present in an amount of from 0.1% to 0.2% by weight of all the components in the SC composition. Pyraxosulfone is present in an amount of from 5% to 7% by weight of all the components in the SC composition. Atrazine is present in an amount of from 40% to 45% by weight of all the components in the SC composition. The surfactant component is comprised of an acrylic graft copolymer and a polyalkylene oxide block copolymer. The acrylic graft copolymer is preferably, for example, TERSPERSE® 2500 Dispersant, available from Huntsman Performance Products and is present in amount of from 2.5% to 3.0% by weight of all the components in the SC composition. The polyalkylene oxide block copolymer is preferably, for example, Atlas™ G-5000, available from Crodia Crop Care and is present in an amount of from 2.5% to 2.75% by weight of all the components in the SC composition. The pH adjuster is preferably an acid, for example, glacial acetic acid, and is present in an amount of from 0.01% to 0.1% by weight of all the components in the SC composition. The anti-freeze agent is preferably propylene glycol and is present in an amount of from 5% to 10% by weight, preferably 5.5% to 6% by weight of all the components in the SC composition. The antifoam agent is preferably a silicone emulsion, for example, DOWCORNING® AF Emulsion available from Dow® Chemical Company and is present in an amount of 0.05% to 0.1% by weight of all the components in the SC composition. The biocide is preferably, for example, KATHON™ CG or LEGEND® MK both available from Dow® Chemical Company or Acticide® MV available from Thor Specialties, Inc., and is present in an amount of from 0.01% by weight to 0.1% by weight of all components in the total composition. The stabilization component is fumed alumina, preferably as an aqueous dispersion that is acidic, for example, AERODISP® W 630, available from Evonik Industries, and is present in an amount of from 0.5% to 2% by weight of all the components in the SC composition.

The weight ratio of fluthiacet-methyl to pyraxosulfone to atrazine can vary over a wide range but is usually in the range of 1:33:284 to 1:40:325.

A particular embodiment of the present invention is a method for the control of unwanted plants comprising applying a pesticidally effective amount of the composition of the present invention to an area where such control is desired.

As used in this specification and, unless otherwise indicated, the term "herbicide" refers to a molecule or combination of molecules that inhibits or otherwise kills unwanted plants, such as, but not limited to, deleterious or annoying weeds, broadleaf plants, grasses and sedges and can be used for crop protection, edifice protection or turf protection. The term "herbicidally effective amount" means an amount necessary to produce an observable herbicidal effect on unwanted plant growth, including the effects of necrosis, death, growth inhibition, reproduction inhibition, inhibition of proliferation, and removal, destruction, or otherwise diminishing the occurrence and activity of unwanted plants.

The terms "ambient temperature" and "room temperature" as utilized herein shall generally mean any suitable temperature found in a laboratory or other working quarter, and is generally neither below about 15° C. nor above about 30° C.

As used herein, "% by weight of components in the composition" includes the wt % of all liquid and solid components in the composition.

The process and compositions of the present invention are further illustrated by the examples below. The examples serve only to illustrate the invention and should not be interpreted as limiting since further modifications of the disclosed invention will be apparent to those skilled in the art. All such modifications are deemed to be within the scope of the invention as defined in the claims.

EXAMPLE 1

Preparation of a Suspoemulsion Concentrate Formulation of Atrazine, Pyroxasulfone and Fluthiacet-methyl with Fumed Alumina as the Stabilization Agent Step A: Atrazine/Pyroxasulfone Suspension Concentrate (SC)

A mixture of 179.90 grams of deionized water, 0.10 grams of glacial acetic acid, 36.00 grams of polyethylene glycol, 0.60 gram of anti foam agent (Dow® Antifoam AF from The Dow Chemical Company), 0.60 gram of a preservative (Kathon™ CG/ICP from The Dow Chemical Company), 14.10 grams of an alkyl EO/PO copolymer nonionic surfactant (Tergitol[lm] XD from The Dow Chemical Company), 20.10 grams of an acrylic graft copolymer surfactant (Tersperse® G-2500 from Huntsman Performance Products), 7.80 grams of an aqueous dispersion of fumed alumina (Aerodisp® W630 from Evonic Industries), 37.50 grams of pyroxasulfone (99.3% purity) and 303.0 grams of Atrazine (97.0% purity) was added to a 1 liter beaker and blended for five minutes at 4500 rpm using a Silverson homogenizer. The mixture was transferred to an Eiger mill and milled for 15 minutes at 3000 rpm, achieving a particle size of D90 <3 μm.

Step B: Fluthiacet-methyl Emulsion in Water (EW)

Fluthiacet-methyl, 12.36 grams (99.1% purity) and 47.50 grams of a nonionic polymeric surfactant (Atlox™ 4914 from Crodia Crop Care) was added to 475.00 grams of an aromatic naphthalene depleted solvent (Aromatic 200 ND from ExxonMobile Chemicals). The mixture was stirred and heated to about 65° C., forming a solution. This solution was added to a warm (about 65° C.) solution of 0.50 gram of glacial acetic acid, 60.00 grams of propylene glycol, 50.00 grams of a polyalkylene oxide block copolymer (Atlas™ G5000 from Crodia Crop Care), 0.50 gram of anti foam agent (Dow® Antifoam AF from The Dow Chemical Company) and 1.00 gram of a preservative (Kathon™ CG/ICP from The Dow Chemical Company) in 353.00 grams of deionized water. This mixture homogenized using a Silverson homogenizer until a uniform mixture was formed.

Step C: Suspoemulsion Concentrate (SE) Formation

A suspoemulsion concentrate was formed by combining 367.82 grams of atrazine/pyroxasulfone SC from Step A with 51.84 grams of the fluthiacet-methyl EW from Step B and 4.67 grams of deionized water. The resultant composition was stirred until a uniform mixture was obtained. The resultant suspoemulsion concentrate composition was evenly distributed into eight ounce glass jars, sealed and stored for stability testing either at an elevated temperature of 54° C. for two weeks. Analysis by High Performance Liquid Chromatography (HPLC) indicated the following after two weeks at elevated temperature: initial analysis—atrazine 42.33%; pyroxasulfone 5.40%; fluthiacet-methyl 0.16%; elevated temperature atrazine 42.48%; pyroxasulfone 5.42%; fluthiacet-methyl 0.16%; indicating that the composition was chemically stable.

Visual inspection of the suspoemulsion concentrate composition at two weeks indicated no phase separation or sedimentation indicating the composition was physically stable.

EXAMPLE 2

Atrazine/Pyroxasulfone Suspension Concentrate (SC) and Fluthiacet-methyl emulsion in Water (EW) preparations with Fumed Alumina as the Stabilization Agent In a manner similar to Step A of Example 1, additional SC compositions containing atrazine and pyroxasulfone were prepared. In a manner similar to Step B of Example 1, additional EW compositions containing fluthiacet-methyl were prepared. Table 2A below summarizes additional SC compositions; Table 2B summarizes additional EW compositions.

TABLE 2A

SC Compositions Containing Atrazine and Pyroxasulfone

| | % by Weight Of Component In SC Composition | | | | | | | | |
|---|---|---|---|---|---|---|---|---|---|
| Component* | 2-1A | 2-2A | 2-3A | 2-4A | 2-5A | 2-6A | 2-7A | 2-8A | 2-9A |
| Pyroxasulfone | 6.25 | 6.25 | 6.25 | 6.41 | 5.90 | 5.90 | 5.15 | 5.15 | 5.90 |
| Atrazine | 50.50 | 50.50 | 50.50 | 52.10 | 50.50 | 50.50 | 44.50 | 44.50 | 50.50 |
| Terg XD | 2.35 | 2.35 | 2.35 | 2.35 | 2.35 | 2.35 | 2.35 | 2.35 | 2.35 |
| Tersp 2500 | 3.35 | 3.35 | 3.35 | 3.35 | 3.35 | 3.35 | 3.35 | 3.35 | 3.35 |
| Aerodisp | 1.30 | 1.30 | 1.30 | 1.30 | 1.30 | 1.80 | 0.50 | 1.25 | 0.90 |
| Acetic Acid Glacial | 0 | 0.05 | 0.10 | 0.10 | 0.10 | 0.10 | 0.10 | 0.10 | 0.10 |
| Glycol | 6.00 | 6.00 | 6.00 | 6.00 | 6.00 | 6.00 | 6.00 | 6.00 | 6.00 |
| Dow AF | 0.10 | 0.10 | 0.10 | 0.10 | 0.10 | 0.10 | 0.10 | 0.10 | 0.10 |
| Kathon | 0.10 | 0.10 | 0.10 | 0.15 | 0.15 | 0.15 | 0.15 | 0.15 | 0.15 |

TABLE 2A-continued

| SC Compositions Containing Atrazine and Pyroxasulfone | | | | | | | | | |
|---|---|---|---|---|---|---|---|---|---|
| | % by Weight Of Component In SC Composition | | | | | | | | |
| Component* | 2-1A | 2-2A | 2-3A | 2-4A | 2-5A | 2-6A | 2-7A | 2-8A | 2-9A |
| Thickener | 0 | 0 | 0 | 0 | 0 | 0 | 0.34 | 0.34 | 0 |
| Water | 30.05 | 30.00 | 29.95 | 28.14 | 30.25 | 29.75 | 37.36 | 36.61 | 30.65 |

Pyroxasulfone 99.3% purity
Atrazine 97% purity
Terg XD = Tergitol ™ XD from The Dow Chemical Company
Tersp 2500 = Tersperse ® 2500 from Huntsman Performance Products
Areodisp = Aerodisp ® W630 from Evonic Industries
Glycol= Propylene glycol
Dow AF = Dow ® Antifoam AF from The Dow Chemical Company
Kathon = Kathon ™ CG/ICP from The Dow Chemical Company
Thickener = Veegum ® Magnesium Aluminum Silicate from R. T. Vanderbilt Company Inc.

TABLE 2B

| EW Compositions Containing Fluthiacet-methyl | | |
|---|---|---|
| | % by Weight Of Component In EC Composition | |
| Component* | 2-2A | 2-2B |
| Fluthiacet-Methyl | 1.236 | 1.236 |
| Aromatic 200ND | 47.500 | 47.500 |
| Atlox | 4.750 | 4.750 |
| Atlas | 5.000 | 5.000 |
| Acetic Acid Glacial | 0.050 | 0.050 |
| Propylene Glycol | 6.000 | 6.000 |
| Biocide | (Kathon) 0.150 | (Acticide) 0.090 |
| Dow AF | 0.050 | 0.050 |
| Thickener | 0.090 | 0 |
| Water | 35.174 | 35.324 |

*Fluthiacet-methyl 99.1% assay
Aromatic 200 ND from ExxonMobile Chemicals
Atlox = Atlox ™ 4914 from Crodia Crop Care
Atlas = Atlas ™ G5000 from Crodia Crop Care
Kathon = Kathon ™ CG/ICP from The Dow Chemical Company
Acticide = Acticide ® MV from Thor Specialties, Inc.
Dow AF = Dow ® Antifoam AF from The Dow Chemical Company
Thickener = Kelzan ® ASX Xanthan Gum form CPKelco A Huber Company

EXAMPLE 3

Preparation of a Suspoemulsion Concentrate Formulation of Atrazine, Pyroxasulfone and Fluthiacet-methyl with Fumed Alumina as the Stabilization Agent Step A: Atrazine/Pyroxasulfone Suspension Concentrate (SC)

A mixture of 2.311 kilograms of deionized water, 7.7 grams of glacial acetic acid, 463.0 grams of polyethylene glycol, 7.7 gram of anti foam agent (Dow® Antifoam AF from The Dow Chemical Company), 6.9 gram of a preservative (Acticide® MV from Thor Specialties, Inc.), 181.4 grams of an alkyl EO/PO copolymer nonionic surfactant (Tergitol™ XD from The Dow Chemical Company), 258.5 grams of an acrylic graft copolymer surfactant (Tersperse® G-2500 from Huntsman Performance Products) was added to a slurry tank and mixed until uniform. Portion wise additions of pyroxasulfone (480.0 grams, 99.3% purity) and Atrazine (3.862.0 kilograms, 97.0% purity) were made to the tank allowing each addition to mix in thoroughly before adding the next portion. The mixture was transferred to an attritor mill and milled, keeping the temperature at less than 30° C., until a particle size of D90 <3 μm was attained. The milled mixture was transferred to a blending tank and 138.9 grams of an aqueous dispersion of fumed alumina (Aerodisp® W630 from Evonic Industries) was added. The mixture was stirred for one hour to provide 6.79 kilograms of a suspension concentrate.

Step B: Fluthiacet-methyl Emulsion in Water (EW)

An organic phase was prepared by adding 141.4 grams of fluthiacet-methyl (99.1% purity) and 544.5 grams of a nonionic polymeric surfactant (Atlox™ 4914 from Crodia Crop Care) to 5.4446 kilograms of an aromatic naphthalene depleted solvent (Aromatic 200 ND from ExxonMobil Chemicals). The mixture was stirred and heated to about 55° C., in a 15 liter jacketed vessel with an in-line homogenizer, forming a solution. An aqueous phase was prepared by adding 5.7 grams of glacial acetic acid, 687.7 grams of propylene glycol, 573.1 grams of a polyalkylene oxide block copolymer (Atlas™ G5000 from Crodia Crop Care), 5.70 gram of anti foam agent (Dow® Antifoam AF from The Dow Chemical Company) and 4.0492 kilograms of deionized water into a mixing vessel and heated at 55° C. until a homogenous mixture was obtained. The warm organic phase was added to the aqueous phase through the recirculation line of an in-line homogenizer. Once the addition was complete, the homogenization continued until a particle size of less than 3 microns at D90 was achieved. The mixture was allowed to cool to room temperature and 10.3 grams of a preservative (Acticide® MV from Thor Specialties, Inc.) was added and stirred until a uniform mixture, about 11.2 kilograms, was obtained.

Step C: Suspoemulsion Concentrate (SE) Formation

A suspoemulsion concentrate was formed by combining 6.658 kiolgrams grams of atrazine/pyroxasulfone SC from Step A with 941.0 grams of the fluthiacet-methyl EW from Step B and 186.0 grams of deionized water. The resultant composition was stirred until a uniform mixture, 7.77 kilograms, was obtained. This suspoemulsion formulation was stored in separate sealed glass containers.

REFERENCE EXAMPLE A

Preparation of a Suspoemulsion Concentrate Formulation of Atrazine, Pyroxasulfone and Fluthiacet-methyl with Fumed Silica as the Stabilization Agent Step A: Atrazine/Pyroxasulfone Suspension Concentrate (SC)

A mixture of 186.8 grams of deionized water, 0.50 gram of glacial acetic acid, 30.00 grams of polyethylene glycol, 0.50 gram of anti foam agent (Dow® Antifoam AF from The Dow Chemical Company), 0.75 gram of a preservative (Kathon™ CG/ICP from The Dow Chemical Company), 11.75 grams of an alkyl EO/PO copolymer nonionic surfactant (Tergitol™ XD from The Dow Chemical Company), 16.75 grams of an acrylic graft copolymer surfactant (Tersperse® G-2500 from Huntsman Performance Products), 2.50 grams of an aqueous dispersion of fumed silica (Aerodisp® W 7512 S from Evonic Industries, a commonly used emulsion stabilizer), 25.75 grams of pyroxasulfone (99.3% purity) and 222.50 grams of Atrazine (97.0% purity) was added to a 1 liter beaker and blended for five minutes at 4500 rpm using a Silverson homogenizer. The mixture was transferred to an Eiger mill and milled for 15 minutes at 3000 rpm, achieving a particle size of D90 <3 μm.

Step B: Fluthiacet-methyl Emulsion in Water (EW)

Fluthiacet-methyl, 18.54 grams (99.1% purity) and 71.25 grams of a nonionic polymeric surfactant (Atlox™ 4914 from Crodia Crop Care) was added to 712.50 grams of an aromatic naphthalene depleted solvent (Aromatic 200 ND from ExxonMoblie Chemicals). The mixture was stirred and heated to about 65° C., forming a solution. This solution was added to a warm (about 65° C.) solution of 0.75 gram of glacial acetic acid, 90.00 grams of propylene glycol, 75.00 grams of a polyalkylene oxide block copolymer (Atlas™ G5000 from Crodia Crop Care), 0.75gram of anti foam agent (Dow® Antifoam AF from The Dow Chemical Company) and 2.25 grams of a preservative (Kathon™ CG/ICP from The Dow Chemical Company) in 527.61 grams of deionized water. This mixture was homogenized using a Silverson homogenizer until a uniform mixture was formed.

Step C: Suspoemulsion Concentrate (SE) Formation

A suspoemulsion concentrate was formed by combining 449.3 grams of atrazine/pyroxasulfone SC from Step A with 50.8 grams of the fluthiacet-methyl EW from Step B and 4.67 grams of deionized water. The resultant composition was stirred until a uniform mixture was obtained. This suspoemulsion formulation was stored in separate sealed glass containers.

EXAMPLE 4

Preparation of an Aqueous Suspension Concentrate Formulation of Atrazine, Pyroxasulfone and Fluthiacet-methyl with Fumed Alumina as the Stabilization Agent A mixture of 308.72 grams of deionized water, 0.72 gram of glacial acetic acid, 46.88 grams of polyethylene glycol, 0.72 gram of anti foam agent (Dow® Antifoam AF from The Dow Chemical Company), 0.72 gram of a preservative (Acticide® MV from Thor Specialties, Inc.), 22.96 grams of an acrylic graft copolymer surfactant (Tersperse® G-2500 from Huntsman Performance Products), 20.88 grams of a polyalkylene oxide block copolymer (Atlas™ G5000 from Crodia Crop Care), 12.32 grams of an aqueous dispersion of fumed silica (Aerodisp® W 7512 S from Evonic Industries, a commonly used emulsion stabilizer), 42.56 grams of pyroxasulfone (99.3% purity), 342.40 grams of Atrazine (97.0% purity) and 1.20 grams of fluthiacet-methyl (99.1% purity) was added to a 2 liter beaker and blended for five minutes at 4500 rpm using a Silverson homogenizer. The mixture was transferred to an Eiger mill and milled until a particle size of D90 <3 μm was achieved. This SC formulation was stored in separate sealed glass containers.

EXAMPLE 5

Physical and Chemical Stability Data

A dilution re-dispersion study was conducted using either 1.0 gram (1%) or 3.0 grams (3%) of the suspoemulsion concentrate compositions from Example 3 and Reference Example A added to 99.0 mL or 97.0 mL of water with either 20 ppm or 500 ppm hardness in a 100 mL Nessler tube. The Nessler tube was sealed with a rubber stopper and the contents mixed by inverting the tube ten times. The test samples so produced were maintained at ambient temperature. Re-suspension assessment of the formulation was performed at 24 hours and the number of inversions needed to produce a homogenous mixture was recorded. Table 4A below summarizes the re-dispersion data.

TABLE 4A

Re-suspension Data From Example 3 and Reference Example A

| | 1% | | 3% | |
|---|---|---|---|---|
| Product | 20 ppm | 500 ppm | 20 ppm | 500 ppm |
| Example 3 | 3 | 3 | 6 | 6 |
| Reference Example A | 6 | 14 | 100 | 100 with film on bottom of tube |

The suspoemulsion concentrate compositions of Example 3 and Example 4 were analyzed for physical and chemical stability at 24hours (Initial), Freeze/Thaw (F/T) cycle (three cycles of two days at minus 30° C./two days at room temperature) and 54° C. for two weeks. The suspoemulsion of Example 3 was also analyzed for physical and chemical stability at one and three months at 50° C. and one month at room temperature. Sample viscosity (centipoise) was measured using a Brookfield RVT viscometer, spindle number 3, spindle speed of 50. Particle size was measured using a particle size distribution analyzer (Horiba Particle Scattering Particle Size Distribution Analyzer LA-910) at D90 (90% of the particles were of the size reported in microns). Percent separation was measured visually by measuring the height of the separated layer and dividing that number by the total height of the container. Analysis for the active ingredients was performed by HPLC analysis on a % by weight basis. These data are summarized in Table 4B below.

TABLE 4B

Physical and Chemical Stability Data For Example 3 Suspoemulsion

| Sample Reference | Viscosity | Particle size | % Separation | Fluthiacet-methyl % by Weight | Pyroxasulfone % by Weight | Atrazine % by Weight |
|---|---|---|---|---|---|---|
| Example 3 Initial | 376 | 1.3 | 0 | 0.15 | 5.40 | 43.00 |
| Example 3 F/T | 432 | 1.2 | 0 | 0.15 | 5.40 | 43.00 |

TABLE 4B-continued

Physical and Chemical Stability Data For Example 3 Suspoemulsion

| Sample Reference | Viscosity | Particle size | % Separation | Fluthiacet-methyl % by Weight | Pyroxasulfone % by Weight | Atrazine % by Weight |
|---|---|---|---|---|---|---|
| Example 3 2 week @ 54° C. | 184 | 2.6 | 0 | 0.15 | 5.39 | 43.28 |
| Example 3 1 month @ 50° C. | 260 | 1.9 | 0 | 0.15 | 5.32 | 43.31 |
| Example 3 1 month @ Room temperature | 342 | 2.0 | 0 | ND | ND | ND |
| Example 3 3 Month @ 50° C. | 150 | 2.3 | 0 | 0.14 | 5.36 | 43.17 |
| Example 4 Initial | 78 | 1.7 | ND | ND | ND | ND |
| Example 4 F/T | 124 | 2.1 | 8.7 | ND | ND | ND |
| Example 4 2 week @ 54° C. | 64 | 2.0 | 8.0 | ND | ND | ND |

As can be seen by the data provided above, physically and chemically stable compositions are formed by the addition of fumed alumina to agricultural compositions such as suspoemulsion formulations and suspension concentrate formulations as compared to similar compositions employing commonly used stabilizers such as fumed silica.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:

1. A suspoemulsion concentrate composition comprising:

i) an aqueous suspension concentrate composition containing pyroxasulfone and atrazine;

ii) an emulsion in water composition containing fluthiacet-methyl; and iii) fumed alumina.

2. The suspoemulsion concentrate composition of claim 1 wherein the aqueous suspension concentrate further comprises one or more of a surfactant component, a pH adjuster, an anti-freeze agent, an antifoam agent, a thickening agent and anti-microbial agent.

3. The suspoemulsion concentrate composition of claim 1 wherein the emulsion in water concentrate further comprises one or more of a surfactant component, a pH adjuster, an anti-freeze agent, an antifoam agent, a thickening agent and anti-microbial agent.

4. The composition of claim 1 wherein the weight ratio of fluthiacet-methyl to pyraxosulfone to atrazine is from 1:33:284 to 1:40:325.

5. A process for the preparation of a suspoemulsion composition comprising:

i) forming an aqueous suspension concentrate composition containing pyroxasulfone and atrazine;

ii) forming an emulsion in water composition containing fluthiacet-methyl;

iii) blending the suspension concentrate and emulsion in water compositions together and iv) adding fumed alumina and blending the mixture to form a homogenous mixture.

6. A process for the preparation of a suspoemulsion composition comprising:

i) forming an aqueous suspension concentrate composition containing pyroxasulfone and atrazine and fumed alumina;

ii) forming an emulsion in water composition containing fluthiacet-methyl;

iii) blending the suspension concentrate and emulsion in water compositions together to form a homogenous mixture.

7. An aqueous suspension concentrate composition comprising:

i) an agriculturally active component comprising fluthiacet-methyl, atrazine and pyroxasulfone;

ii) a surfactant component comprising an acrylic graft copolymer and a polyalkylene oxide block copolymer;

iii) an antifoam agent;

iv) a biocide;

v) a pH adjusting agent;

vi) an antifreeze agent; and vii) fumed alumina.

* * * * *